United States Patent
Baura (10) Patent No.: US 7,639,146 B2
(45) Date of Patent: Dec. 29, 2009

(54) BLINK MONITOR FOR DETECTING BLINK OCCURRENCE IN A LIVING SUBJECT

(76) Inventor: Gail D. Baura, 1920 Froude St., San Diego, CA (US) 92107

( * ) Notice: Subject to any disclaimer, the term of this patent is extended or adjusted under 35 U.S.C. 154(b) by 131 days.

(21) Appl. No.: 11/235,373

(22) Filed: Sep. 26, 2005

(65) Prior Publication Data

US 2006/0077064 A1    Apr. 13, 2006

Related U.S. Application Data

(60) Provisional application No. 60/614,208, filed on Sep. 29, 2004, provisional application No. 60/646,045, filed on Jan. 20, 2005.

(51) Int. Cl.
G08B 23/00    (2006.01)
(52) U.S. Cl. ..................... 340/573.1; 340/575
(58) Field of Classification Search ............. 340/573.1, 340/575, 576, 544, 545, 558, 546, 382, 383, 340/386
See application file for complete search history.

(56) References Cited

U.S. PATENT DOCUMENTS

| | | | |
|---|---|---|---|
| 3,945,376 A | 3/1976 | Kuehnegger | |
| 4,359,724 A | 11/1982 | Zimmerman et al. | |
| 4,725,824 A | 2/1988 | Yoshioka | |
| 4,776,345 A | 10/1988 | Cohen et al. | |
| 5,349,963 A | 9/1994 | Eskelinen | |
| 5,491,492 A | 2/1996 | Knapp et al. | |
| 5,566,067 A | 10/1996 | Hobson et al. | |
| 5,601,088 A | 2/1997 | Swanson et al. | |
| 5,605,157 A | 2/1997 | Panescu et al. | |
| 5,813,993 A | 9/1998 | Kaplan et al. | |

(Continued)

FOREIGN PATENT DOCUMENTS

EP    1 004 268 A2    5/2000

OTHER PUBLICATIONS

Goodale, Carol, "*Getting Smart About Getting Around*", IEEE, The Institute, vol. 28, No. 2, Jun. 2004.

(Continued)

*Primary Examiner*—Daryl Pope
(74) *Attorney, Agent, or Firm*—Knobbe, Martens, Olson & Bear LLP (57) ABSTRACT

Embodiments of the present disclosure include a blink monitor for detecting blink occurrence in a living subject. For example, a blink sensor comprising a snap or tab electrode is positioned over one or more eye muscles known to assist in closing the eye. The electrode detects the electrical current in the muscle(s) and transmits a signal representative of the electrical current to a signal processing device. The device processes the signal to determine the occurrence of a blink, thereby producing an accurate blink electromyogram (EMG). The device and/or a caregiver may advantageously monitor the blink EMG, before and/or after occurrence processing, to determine the onset or actual occurrence of a patient condition. In an embodiment, the device monitors the blink EMG to determine the onset or occurrence of drowsiness in, for example, a driver, pilot, captain, doctor, soldier, or the like. In an embodiment, a caregiver monitors the blink EMG for one or more muscles in one or both eyes to determine the onset or occurrence of eye disease, such as, for example, strabismus.

35 Claims, 5 Drawing Sheets

U.S. PATENT DOCUMENTS

| | | | |
|---|---|---|---|
| 5,942,979 A | | 8/1999 | Luppino |
| 5,982,287 A | | 11/1999 | Brannen et al. |
| 5,999,846 A | * | 12/1999 | Pardey et al. ............... 600/544 |
| 6,032,072 A | * | 2/2000 | Greenwald et al. .......... 600/544 |
| 6,033,073 A | * | 3/2000 | Potapova et al. ............ 351/211 |
| 6,076,011 A | | 6/2000 | Hoover |
| 6,163,281 A | * | 12/2000 | Torch .......................... 341/21 |
| 6,265,978 B1 | | 7/2001 | Atlas |
| 6,285,899 B1 | | 9/2001 | Ghaem et al. |
| 6,366,813 B1 | | 4/2002 | DiLorenzo |
| 6,386,706 B1 | * | 5/2002 | McClure et al. ............. 351/237 |
| 6,452,081 B1 | * | 9/2002 | Ravagni et al. ........... 84/477 R |
| 6,470,893 B1 | | 10/2002 | Boesen |
| 6,496,705 B1 | | 12/2002 | Ng et al. |
| 6,496,724 B1 | | 12/2002 | Levendowski et al. |
| 6,497,658 B2 | | 12/2002 | Roizen et al. |
| 6,553,252 B2 | | 4/2003 | Balkin et al. |
| 6,575,902 B1 | | 6/2003 | Burton |
| 6,597,944 B1 | | 7/2003 | Hadas |
| 6,625,485 B2 | | 9/2003 | Levendowski et al. |
| 6,643,541 B2 | | 11/2003 | Mok et al. |
| 6,678,551 B2 | | 1/2004 | Maalouf et al. |
| 6,898,460 B2 | | 5/2005 | Hoctor et al. |
| 7,231,245 B2 | * | 6/2007 | Greenwald et al. .......... 600/544 |
| 2004/0015096 A1 | | 1/2004 | Mok et al. |
| 2004/0143170 A1 | | 7/2004 | DuRousseau |
| 2005/0096513 A1 | | 5/2005 | Ozguz et al. |
| 2005/0131288 A1 | | 6/2005 | Turner et al. |
| 2006/0004298 A1 | * | 1/2006 | Kennedy et al. ............ 600/546 |
| 2006/0058590 A1 | * | 3/2006 | Shaw et al. ................. 600/301 |
| 2007/0282172 A1 | | 12/2007 | Toumazou et al. |

OTHER PUBLICATIONS

Jensen, Cheryl, "*Autos on Monday/Technology; Reminder From the Car: Stay Inside the Lines*", The New York Times, Automobiles, Jan. 24, 2005.

http://www.attentiontechnology.com/index.html, "Driver Fatigue is the #1 Cause of Catastrophic Truck Accidents", 1 page downloaded and printed from the World Wide Web on or about Aug. 9, 2004.

http:///www.attentiontechnology.com/pro.html, "An Eye-Opening Course to Prevent Drowsy Driving", 1 page downloaded and printed from the World Wide Web on or about Aug. 9, 2004.

http://www.attentiontechnology.com/con.html, "Contact Us", 1 page downloaded and printed from the World Wide Web on or about Aug. 9, 2004.

http://www.attentiontechnology.com/pro-per.html, "The Most Reliable and Valid Determination of a Driver's Alertness Level", 1 page downloaded and printed from the World Wide Web on or about Aug. 9, 2004.

http://www.attentiontechnology.com/pro-buy.html, "For Your Truck on Your Fleet", 1 page downloaded and printed from the World Wide Web on or about Aug. 9, 2004.

Bursztyn, J. et al., "*Alternating hemiplegia of childhood and oculomotor anomalies*", Journal Francais D"Ophtamologie, vol. 23, No. 2, pp. 161-164, Feb. 2000.

Kaneko, Kenichi et al., "*Spontaneous Blinks As A Criterion Of Visual Fatigue During Prolonged Work On Visual Display Terminals*", Perceptual and Motor Skills, vol. 92, No. 1, pp. 234-250, Feb. 2001.

Kumaran, M.S. et al., "*Wavelet decomposition of the blink reflex R2 component enables improved discrimination of multiple sclerosis*", Clinical Neurophysiology, vol. 11, No. 5, pp. 810-820, May 2000.

Ramanan, S.V. et al., "*A Novel Wavelet Based Technique for Detection and De-Noising of Ocular Artifact in Normal and Epileptic Electroencephalogram*", Communication Circuits and Systems, vol. 12, pp. 1027-1031, Jun. 2004.

PCT International Search Report, App. No. PCT/US 2005/034843, Dated: Feb. 21, 2006, 3 pages.

\* cited by examiner

BLINK MONITOR FOR DETECTING BLINK OCCURRENCE IN A LIVING SUBJECT

PRIORITY CLAIMS

The present application claims a priority benefit of U.S. Provisional Pat. App. Ser. Nos. 60/614,208, filed Sep. 29, 2004, entitled "Apparatus and Method for Determining Drowsiness in a Living Subject," and 60/646,045, filed Jan. 20, 2005, entitled "Apparatus and Method for Ophthalmology Monitoring in a Living Subject." The foregoing disclosure is expressly incorporated herein by reference.

BACKGROUND OF THE INVENTION

1. Field of the Invention

The present disclosure relates to the field of patient or driver monitoring. More specifically, the invention relates to the acquisition and processing of a blink electromyogram (EMG).

2. Description of the Related Art

The onset and occurrence of drowsiness has been long a problem for drivers. Studies indicate that fatigue could be a significant factor in the 100,000 U.S. commercial/passenger vehicle crashes per year. For example, some estimate that fatigue is a factor in approximately fifteen percent of fatal large truck-related crashes. In a 2005 study conducted by the Insurance Institute of Highway Safety, forty two percent (42%) of large truck drivers drove while sleepy during the previous week before being surveyed.

To combat this problem, the automobile industry developed several technologies to attempt to detect errant driving behavior. For example, lane departure systems, such as that disclosed in U.S. Pat. No. 6,930,593, often include a camera mounted near the interior rear view mirror that views the road ahead and detects lane markings. When the system determines that the vehicle is drifting out of its lane, a warning buzzer sounds and an icon may flash on the instrument panel. Embodiments of these types of systems are found at least in various Infiniti M sedans and were in part developed by Valeo and Iteris. However, lane departure systems usually require minimum speeds and a view of well marked lane markings. These system often struggle on roads with worn paint and roads covered with dirt, snow, rain, or the like, or in actual storm or wind conditions. Moreover, such systems often confuse desired lane changes, inattentive driving, and drowsiness.

Other systems turn the camera on the driver. Originally, because image processing of the face was difficult, Carnegie Mellon researcher Richard Grace transmitted a wavelength of light to a driver's eye from the dashboard, and received the reflected light as disclosed in U.S. Pat. No. 6,082,858. Grace focused on monitoring the percentage of time a driver's eye is closed, or PERCLOS. The PERCLOS monitor alarms when it detects a PERCLOS pattern that Grace recognizes as being associated with a driver getting drowsy. However, such cameras include significant drawbacks of being unusable and/or inaccurate when a driver wears sunglasses, subject to significant errors, and subject to interference when objects are placed between the emitter or lens and the face of the driver.

In an attempt to correlate a physiologic signal with drowsiness, Ulrika Svensson explored the use of the electrooculogram (EOG) in her thesis at the University of Linkoping. In general, the EOG comprises a record of the standing voltage of the retina, the layers of cells at the back of the eye that conduct vision processing. The EOG is correlated with eyeball movement and obtained by electrodes placed on the skin above and below, or left and right of, the eye. In Svensson's drowsiness system, the use of two sensors complicate blink monitor processing through the addition of noise. Further, because Svensson employs primitive curve fit-, threshold-type algorithms for detection, the system has difficulty accommodating motion artifact or a large range of EOG morphologies.

SUMMARY OF THE INVENTION

Accordingly, a need exists for a reliable blink sensor monitor for detecting blink occurrences in a living subject, such as a driver or a patient. Therefore, the present disclosure includes embodiments of systems and methods for acquiring and analyzing an accurate blink electromyogram (EMG). For example, snap or tab electrodes may advantageously be positioned over one or more muscles of one or both eyes, where the muscles are known to assist in closing the eye. The electrodes detect electrical current in the muscle(s) and transmits signal(s) representative of the electrical current to a signal processing device. The device processes the signal to determine the occurrence of a blink.

The signal processing device and/or a caregiver may advantageously monitor the short or long trending of the blink EMG, before and/or after the foregoing blink occurrence processing, to determine the onset or actual occurrence of a patient condition. In an embodiment, the device monitors the blink EMG to determine the onset or occurrence of drowsiness in, for example, people who need to be attentive, such as, for example, a driver, pilot, captain, doctor, soldier, or the like. In another embodiment, the device monitors the blink EMG for one or more muscles in one or both eyes to determine the onset or occurrence of eye diseases, such as, for example, strabismus (more commonly known as crossed-eyes where a person can not align both eyes simultaneously under normal conditions).

Based on the foregoing, an aspect of the disclosure includes an apparatus for measuring the drowsiness of a living subject. For example, the apparatus comprises a system having one or two electrode pairs, an amplifier for scaling the measured voltage between each electrode pair, an analog-to-digital converter for digitizing the voltage, a transmitter or transceiver for sending the digital voltage, a miniature battery or other power source for powering these components, and a receiver for sensing the amplified voltage. The individual snap or tab electrodes in each electrode pair are spaced using a predetermined distance, such as, for example zero (0) to two (2) or more cm, preferably one (1) cm. Use of this predetermined distance may advantageously provide a stable range of measured voltages across a patient population. Moreover, use of the range provides that when a voltage is measured outside this range, it may advantageously be determined that the electrode pair is disconnected from the driver or patient. The electrode pairs may advantageously be placed at locations below the lower eyelash of the subject, on both the right and left sides, or the like. The transmitter/receiver pair operate at a convenient frequency, such as one within the Industrial Scientific and Medical band, or other acceptable bands recognizable to one of ordinary skill in the art from the disclosure herein.

Another aspect of the disclosure includes a method of monitoring drowsiness of a living subject. The method generally comprises analyzing one, both separately, the mean, or other advantageous combination of the two blink sensor signals to determine drowsiness. In an embodiment, discrete wavelet transforms can advantageously be used to identify the onset of each blink and drowsiness parameters of each blink. The drowsiness parameters may be input to a fuzzy model to determine when drowsiness is present. In one exemplary embodiment, Haar detail coefficients can advantageously be used to isolate blink onset, generally characterized by high frequency blinking, and Haar approximation coefficients can be used to isolate drowsy blink-blink intervals, generally characterized by different low frequency content than alert blink-blink intervals. The decision as to whether the interval is associated with awake or drowsy can be made using a linguistic fuzzy model.

Another aspect of the disclosure includes a drowsiness module adapted to determine drowsiness. The module may advantageously comprise a receiver adapted to sense blink sensor signals, processing circuitry that outputs a drowsiness decision, and an interface to a host or monitoring device. In one exemplary embodiment, the module of the present invention comprises a receiver that sends blink sensor signals to a processor-based system, including program and data memory capable of implementing processing algorithms, such as, for example, those described herein. In an embodiment, the drowsiness decision can be communicated via a standard hospital communication protocol, customized manufacturer protocol, or the like to a hospital patient monitor. In another embodiment, a receiver sends blink sensor signals to a processor-based system, including program and data memory capable of communication via a cellular standard protocol to an emergency system. Yet another embodiment of the drowsiness module includes an EMG module apparatus, comprising a receiver, digital processor-based system, and an interface. The EMG module apparatus can advantageously be configured to operate in conjunction with an intelligent vehicle system. In yet another embodiment of the drowsiness module, an EMG module comprises a plug-in module that communicates with a host device such as a personal computer or dedicated display.

Yet another aspect of the disclosure includes a drowsiness monitor that interfaces to other devices. For example, a standalone drowsiness monitor comprises a receiver that sends received blink sensor signals to a digital processor-based device adapted to process EMG and other signals derived from one or more living subjects. In response to the drowsiness decision, the monitor advantageously outputs signals and alarms to its own display, the display of supervising personnel, emergency services, or the like.

Yet another aspect of the disclosure includes a software environment adapted for use with the aforementioned drowsiness monitor or module. In one exemplary embodiment, the software environment includes initialization, operating, and processing modules adapted to instruct a processing device to perform various boot-up, signal processing, communication, and error detection functions.

Yet another aspect of the disclosure includes a method of determining ophthalmology disorders in a living subject. For example, the method generally comprises analyzing blink sensor signals indicative of the electrical activity in the muscles of both eyes to determine differences between the sensor signals. Discrete wavelet transforms can advantageously identify the onset of each blink or focus response and ophthalmology disorder parameters between each blink or focus response. These disorder parameters can be input into a fuzzy model to classify the disorder. In an embodiment, Haar detail coefficients can advantageously be used to isolate the onset of blink or focus response and onset timing differences, generally characterized by high frequency blinking, and Haar approximations coefficients can be used to isolate muscle stimulus intervals, which include different low frequency content. The parameters are input for determining strabismus, or eye misalignment. Strabismus affects about 3% of the U.S. population, and, if not treated in infants, may lead to disabling double vision, loss of depth perception, and visual loss. Although the mechanism for strabismus is under review, various opinions hold that abnormalities of the extraocular muscles cause the eyes to move in abnormal directions. These abnormalities may be distinguishable in the blink EMG. The decision for ophthalmology disorder classification can be made using a linguistic fuzzy model.

Yet another aspect of the disclosure includes an ophthalmology module comprising a receiver that sends received blink sensor signals to a processor-based device adapted to process blink and other signals derived from one or more living subjects. In response to ophthalmology disorder classification, the module outputs signals and alarms to a display. The module also may advantageously communicate to, for example, a centralized accounting system. The communication may advantageously be over one or more communication networks including computer, telephone, and cellular networks. In an embodiment, the module informs the accounting system of information desired by the same, such as, for example, a number of disorders classification attempts, patient information and data, or the like. Thus, the module may advantageously be adapted for fee-per-use or fee-per-function. In an embodiment, the determination of strabismus is performed by the module. In other embodiments, the module in concert with a caregiver determines the onset, occurrence, and/or severity of strabismus or other disorder.

Further aspects of the disclosure include a method of determining a patient condition including at least one of drowsiness and ocular disorder. The method comprises receiving at least one signal from a sensor capable of detecting electrical activity in one or more muscles in a body of a person, the electrical activity being indicative of a blink occurrence, determining which data from the at least one signal represents the blink occurrence, and evaluating the blink occurrence data to determine an onset or actual occurrence of a patient condition, wherein the patient condition includes at least one of drowsiness and an ocular disorder. Moreover, an aspect of the disclosure includes a device for identifying a blink occurrence within a blink electromyogram (EMG). The device comprises an electrode pair configured to be positioned with respect to one or more muscles used to blink at least one eye in order to output a signal indicative of a changing biopotential associated with the one or more muscles and a processing device configured to receive the signal and identify blink occurrences within the signal.

Yet another aspect includes a blink monitoring system comprising a sensor comprising an electrode pair capable of outputting a signal indicative of a biopotential related to blink occurrences, a transmitting device capable of wirelessly transmitting the signal, and a flexible circuit housing the electrode and the transmitting device. The system further comprises a monitor capable of determining where the blink occurrences appear in the signal. Other aspects include a monitor for monitoring the alertness of a person comprising a receiver configured to receive data indicative of a blink electromyogram (EMG) of a person, a processor configured to determine blink occurrences within the blink EMG and evaluate the blink occurrences to determine an onset or occurrence of diminished alertness, and an alarm signal capable of activating an alarm configured to rectify the diminished alertness in the person.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

The following drawings and the associated descriptions are provided to illustrate embodiments of the present disclosure and do not limit the scope of the claims.

FIG. 7(*a*) illustrates a graph of a typical ECG signal.

FIG. 7(*b*) illustrates a graph of a blink EMG signal obtained from a subject in an alert state, according to an embodiment of the disclosure.

FIG. 7(*c*) illustrates a graph of a blink EMG signal obtained from the same subject, but in a drowsy state, according to an embodiment of the disclosure.

DETAILED DESCRIPTION OF THE PREFERRED EMBODIMENT

Embodiments of the present disclosure include a blink monitoring system for detecting blink occurrences in a living subject. For example, a blink sensor communicates to a blink monitor a signal indicative of electrical current detected in one or more muscles of the eye. The blink monitor processes the signal to determine a blink occurrence. Moreover, the blink monitor and/or a caregiver may advantageously monitor a long or short trend of blink occurrences to determine the onset or actual occurrence of a patient condition. In an embodiment, the blink monitor monitors the blink occurrences to determine the onset or occurrence of drowsiness in, for example, a driver. In another embodiment, the blink monitor monitors the blink occurrences to determine the onset or occurrence of eye disorder, such as, for example, strabismus.

As used herein, the term "processor" and "digital processor" are meant to have their ordinary broad meaning to an artisan, including, for example, digital signal processors (DSPs), reduced instruction set computers (RISC), general-purpose (CISC) processors, microprocessors, application-specific integrated circuits (ASICs), or the like. Such digital processors may be contained on a single unitary IC die, or distributed across multiple components.

As used herein, the terms "monitor" and "monitoring device" are meant to have their ordinary broad meaning to an artisan, including, for example, generally to refer to devices adapted to perform monitoring, display, user interface, and/or control functions. Such devices may be dedicated to a particular function, or multi-purpose devices adaptable to performing a variety of functions and/or interfacing with a number of functional modules.

As used herein, the term "electromyogram" or "EMG" are meant to have their ordinary broad meaning to an artisan, including, a record of the electrical activity of muscles. For example, when muscles are active, they produce an electrical current that is generally proportional to the level of the muscle activity. EMGs have generally been employed in the medical industry to detect abnormal muscle electrical activity that can occur in patients having various diseases and conditions, including muscular dystrophy, inflammation of muscles, pinched nerves, peripheral nerve damage (damage to nerves in the arms and legs), amyotrophic lateral sclerosis (ALS) (also known as Lou Gehrig disease), myasthenia gravis, disc herniation, and others. EMGs are generally acquired through surface electrodes placed on (not into) the skin overlying the muscle to detect the electrical activity of the muscle. Intramuscular EMGs (the most commonly used type) involve inserting a needle electrode through the skin into the muscle to detect the electrical activity therein.

To facilitate a complete understanding of the invention, the remainder of the detailed description describes the invention with reference to the drawings.

Figure 1:
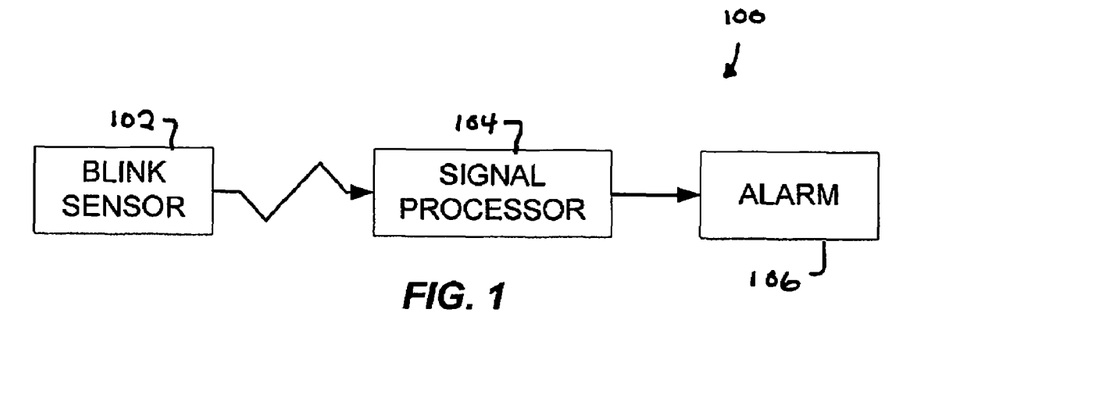
FIG. 1 illustrates an exemplary block diagram of a blink monitoring system according an embodiment of the disclosure.

FIG. 1 illustrates an exemplary block diagram of a blink monitoring system 100 according an embodiment of the disclosure. The system 100 includes a blink sensor 102 communicating one or more signals indicative of electrical activity of one or more muscles usable to close the eye, usable to indicate an eye closure, or the like, to a signal processor 104. In an embodiment the blink sensor 102 comprises one or more snap or tab electrode pairs capable of measuring a voltage between the terminals of the pair, although a skilled artisan may recognize from the disclosure herein a variety of potential blink sensors capable of providing the one or more signals to the monitor 104. In an embodiment, gels may be used to assist in the conductivity between the skin and the electrode pair(s). In an embodiment, the blink sensor 102 wirelessly communicates with the signal processor 104.

The signal processor 104 comprises a processor capable of performing signal processing methodologies on the input signal data. As will be understood by an artisan from the disclosure herein, the processor 104 may include program and data memory, may access computer readable memory, or the like to execute one or more software modules, instruction sets, programs or the like. In an embodiment, the processor executes instructions for wavelet and fuzzy model processing on the signal(s) received from the blink sensor 102 to determine blink occurrences from within the signal(s). The signal processor may output a variety of advantageous information, including, for example, a signal indicative of the received signal(s), one or more of the received signals, the blink occurrences in the form of an accurate blink EMG, a determination of the onset or occurrence of drowsiness or optical disorders, or the like.

FIG. 1 also shows the processor 104 communicating with an alarm 106. Upon determination of the onset or occurrence of a patient condition, the processor 104 may advantageously instruct the alarm 106 to provide an audio or visual indication of the detected condition, a control instruction, or the like. For example, the alarm 106 may include an audio and/or visual signal to a driver that he or she is showing signs of drowsiness, that he or she should no longer drive, or the like. The alarm 106 may advantageously contact a control station, management personnel, emergency personnel, police, or the like, to encourage the driver to rest. Moreover, the alarm 106 may be part of a multi-parameter patient monitoring system.

Figure 2:
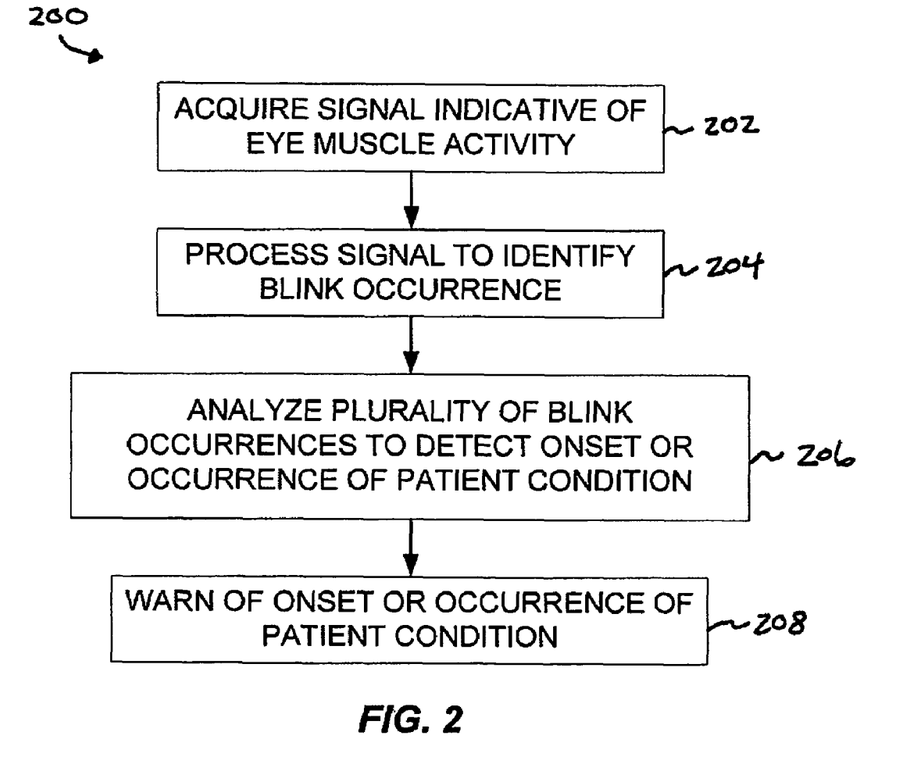
FIG. 2 illustrates an exemplary flow chart of a blink detection process performed using the blink monitoring system of FIG. 1, according to an embodiment of the disclosure.

FIG. 2 illustrates an exemplary flow chart of a blink detection process 200 performed using the blink monitoring system 100 of FIG. 1, according to an embodiment of the disclosure. As shown in FIG. 2, the process 200 comprises acquiring a signal indicative of eye muscle activity (block 202), processing the signal to identify one or more blink occurrences (block 204), analyzing the occurrences to detect the onset or occurrence of a patient condition (block 206), and outputting a result of the analysis (block 208). In an embodiment discussed in further detail below, the processing of the signal includes wavelet filtering and scaling, and a fuzzy model to identify signal segments that correspond to blink occurrences.

Figure 3:
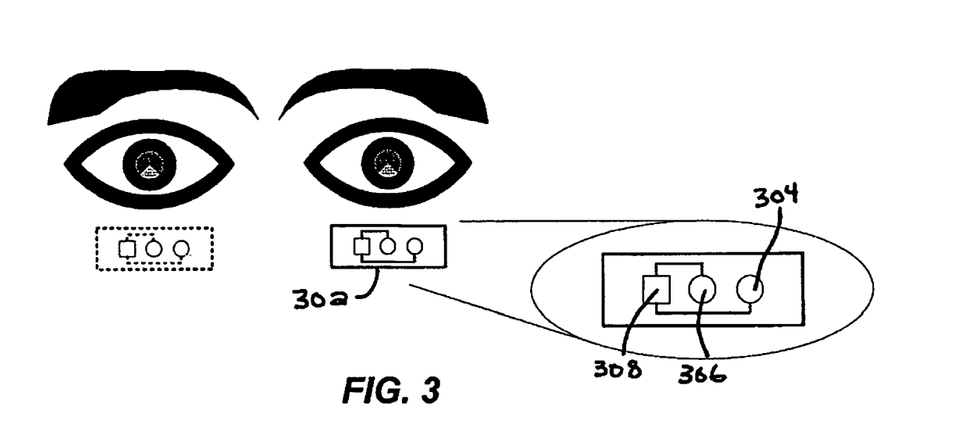
FIG. 3 illustrates an exemplary block diagram of an application of a blink sensor according an embodiment of the disclosure.

FIG. 3 illustrates an exemplary block diagram of an application of a blink sensor 302 according an embodiment of the disclosure. As shown in FIG. 3, the blink sensor 303 comprising a tab electrode may be placed beneath a lower eyelash and around the eye socket area of the right or left eye. As shown in the exploded view, the tab sensor 302 may include two terminals of two electrodes 304, 306, electrically communicating with a processor or controller device 308. In an embodiment, the processor 308 conditions the biopotential signal detected across the electrodes 304, 306. For example, the processor 308 may perform some or all of the following signal conditioning: amplification, noise filtering, and conversion to digital data. In an embodiment, the processor 308 wireless communicates the digitized signal to a pickup receiver.

In an embodiment, the electrodes in each electrode pair are spaced using a predetermined distance, such as, for example about zero (0) to about two (2) or more cm. In a preferable embodiment, the electrode pair are spaced about one (1) cm from one another. Use of this predetermined distance advantageously provides a stable range of measured voltages across a patient population. Moreover, use of the range provides that when a voltage is measured outside this range, it may advantageously be determined that the electrode pair is disconnected from the driver or patient.

Figure 7A:
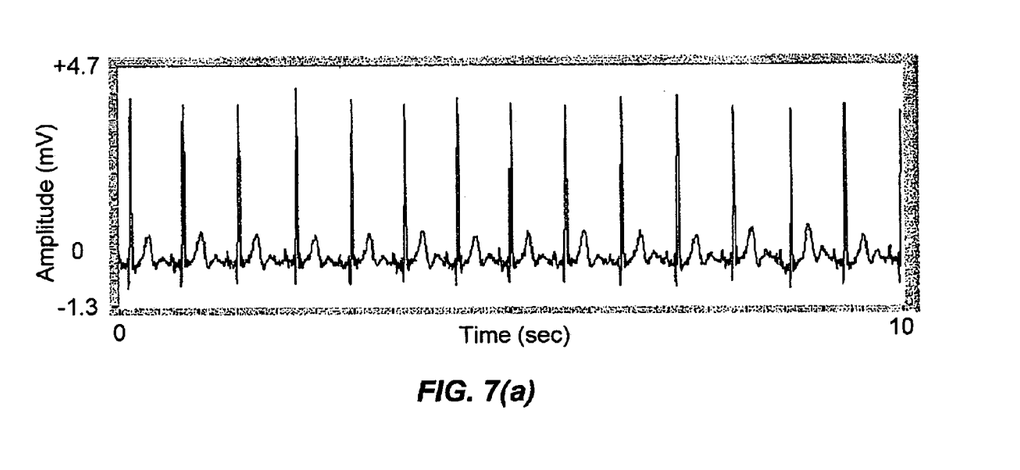
Figure 7B:
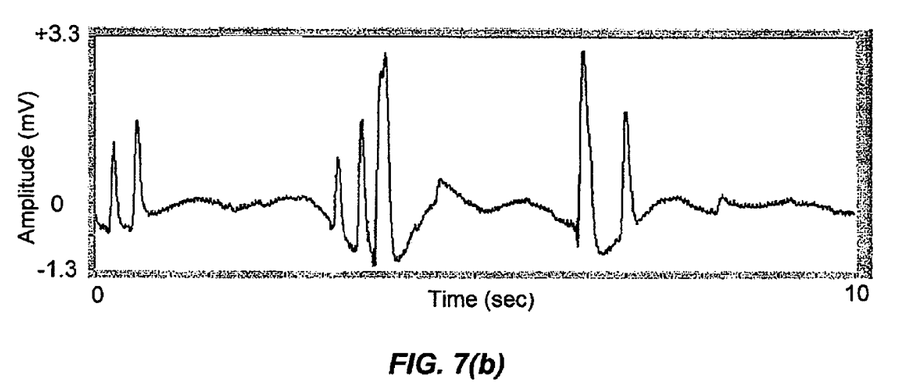

Use of a comparable snap electrode has been shown to produce signal data roughly comparable in quality and amplitude as more typically electrode-monitored muscles. For example, FIG. 7(a) illustrates a graph of a typical ECG signal. As shown in FIG. 7(a), the ECG signal shows a strong heartbeat with an excursion range of about +/− five (5) mV. As shown, the heartbeat reaches a positive amplitude of approximately four (4) mV. As a favorable comparison illustrating the viability of a tab or snap electrode for monitoring eye muscles, FIG. 7(b) illustrates a graph of a blink EMG signal from an eye muscle according to an embodiment of the disclosure exhibiting a similar excursion range of about +/− five (5) mV. In particular, the blink EMG includes a positive amplitude of about three (3) mV.

Figure 4:
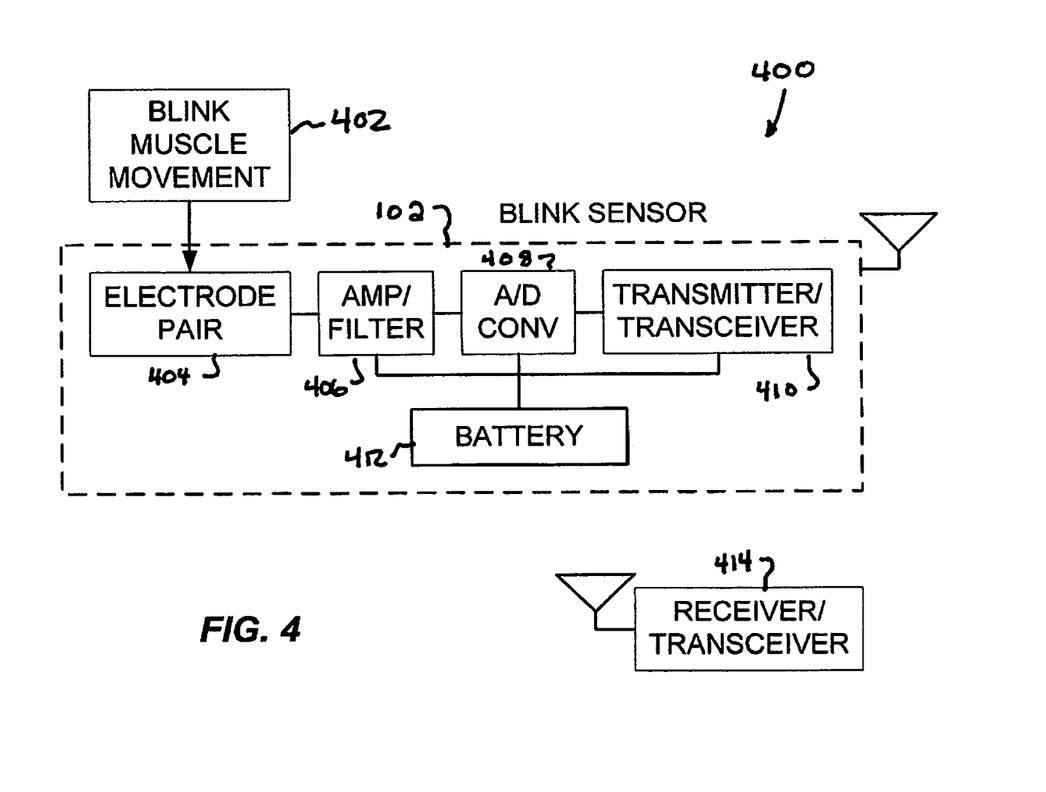
FIG. 4 illustrates an exemplary block diagram of a blink monitoring system, including an embodiment of the blink sensor of FIG. 1, according an embodiment of the disclosure.

FIG. 4 illustrates an exemplary block diagram of the blink monitoring system 400, including an embodiment of the blink sensor 102 of FIG. 1, according an embodiment of the disclosure. As shown in FIG. 4, the sensor 102 includes an electrode pair 404 communicating with an amplifier and/or filter 406, an analog-to-digital converter 408, and in a wireless embodiment, a transmitter 410. The amplifier 406, converter 408 and transmitter 410 may advantageously be powered by power source 412, such as, for example, a battery.

In an embodiment, the electrode pair 404, located beneath the lower eyelash of the right or left eye (although an artisan will recognize from the disclosure herein other locations may be substituted with equivalent/acceptable success) comprises a typical snap- or tab-style electrode. The electrode pair 404 detect an EMG voltage resulting from local muscle activity present during blinking 402. Using a predetermined distance between electrode terminals provides a stable range of measured voltages across a patient population. When a voltage is measured outside this range, it can be determined that the electrode pair is disconnected from the patient.

The gain of the EMG is increased using an amplifier, which may include the anti-aliasing lowpass filter 406. The amplified EMG is then digitized using the A/D converter (ADC) 408. The digitized signal is transmitted by the transmitter 410 at a convenient frequency, such as one within the Industrial Scientific and Medical band. In one embodiment, the amplifier 406, A/C 408, battery 412, and transmitter 410 are co-located on the tab electrode 404 using a flex circuit recognizable to an artisan from the disclosure herein. The receiver 414 senses the digitized signal within an EMG monitor or module An artisan will recognize from the disclosure herein that the analog signal may be transmitted to the receiver 414, that some signal processing may occur using electronics on the monitor, the electrode, combinations of the same, or the like.

Figure 5:
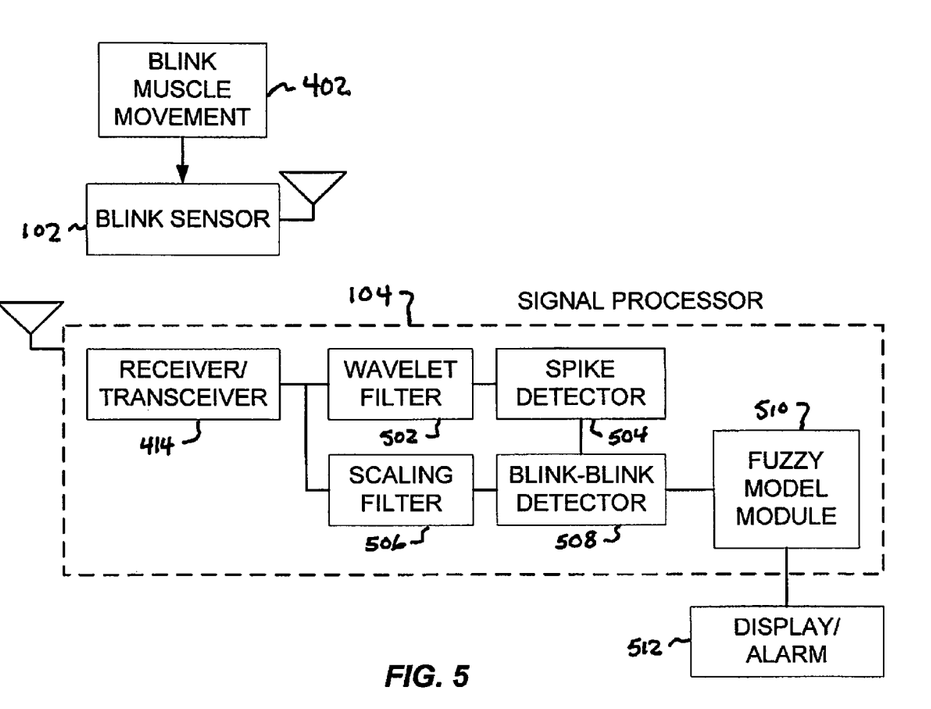
FIG. 5 illustrates an exemplary block diagram of a blink monitoring system, including an embodiment of the signal processor of FIG. 1, according an embodiment of the disclosure.

FIG. 5 illustrates an exemplary block diagram of a blink monitoring system 500, including an embodiment of the signal processor 104 of FIG. 1, according an embodiment of the disclosure. As shown in FIG. 5, the signal processor 500 may include the receiver 414 providing the signal to a wavelet filter 502 and a scaling filter 506. The wavelet filter 502 forwards the filtered signal to a spike detector 504. The spike detector 504 and the scaling filter 506 forward signals to a blink-blink detector 508 which forwards the resulting signal to a fuzzy model analysis module 510. The fuzzy model analysis module 510 outputs results to a display and/or alarm device 512.

Figure 7C:
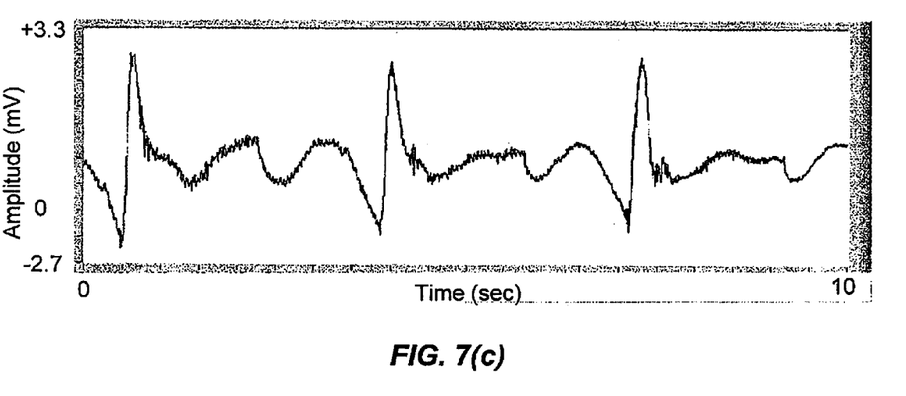

In an embodiment, one, both, the mean, or other combination of two EMGs resulting from blinking are analyzed using discrete wavelet transforms. A "discrete wavelet transform" as used herein is meant to have its broad ordinary meaning to an artisan, including being a time-scale representation of an input signal that is obtained by convolving the signal with a wavelet or scaling filter at a particular scale. Various wavelet and scaling filters are utilized (as discussed below) to emphasize certain features of interest associated with the EMG waveforms obtained from electrodes positioned under the lower eyelash. The wavelet filter 502 acts as a highpass filter to obtain wavelet transform detail coefficients. The wavelet scaling filter 506 acts as a lowpass filter to obtain wavelet transform approximation coefficients. Convolution of the input signal(s) with the wavelet filter 502 identifies each EMG spike cluster, which represents the onset of a blink. The input signal(s) are also convolved with the scaling filter 506. The resulting approximation coefficients are separated into blink-blink intervals, using the detected blink onsets. Detection of characteristic low frequency morphologies by the blink-blink detector 508 leads to the output of drowsiness parameters. These drowsiness parameters are analyzed using the fuzzy model 510. A "fuzzy model" as used herein is meant to have its broad ordinary meaning to an artisan and including reference to a nonlinear, time-invariant system operator that is sufficiently complex that it cannot be easily summarized with conventional mathematical equations. Fuzzy models are typically used for pattern recognition, modeling, and prediction. Based on the current values of drowsiness parameters, each blink-blink interval is judged by the fuzzy model as being as either aware or drowsy. An artisan will recognize that clinical data will advantageously assist in determining the best or most appropriate particular input membership functions, rule base inference, and output membership functions. The clinical data may advantageously include EMG patterns determined to correspond to particular patient conditions, including the onset or occurrence of drowsiness or ophthalmology disorders. For example, FIG. 7(b) illustrates a blink EMG obtained from an alert subject, while FIG. 7(c) illustrates a blink EMG from the same subject, but in a drowsy state In one exemplary embodiment, the wavelet filter 502 employs Haar detail coefficients to isolate blink onset, which is high frequency and shaped like one or more spikes. The filter 502 also employs Haar approximation coefficients to isolate drowsy blink-blink intervals. A linguistic fuzzy model then classifies the different low frequency content of alert versus drowsy blink-blink intervals. The low frequency distinctions between alert versus drowsy blink-blink intervals become apparent from analysis of substantial numbers (i.e., several hundred) of patient blink waveforms. Analysis of these blink waveforms will also determine the fuzzy model input membership functions, rule base inference, and output membership functions. For example, one set of input membership functions for the fuzzy model could be based on the global minimum of the Haar wavelet approximation coefficients, calculated between two blink onsets. In concert with a second set of input membership functions and a rule base inference table, a detection decision would be generated (on/off), based on one set of output membership functions. It will be recognized, however, that other types of wavelets (such as the family of biorthogonal or Daubechies wavelets) could be substituted for or used in conjunction with the Haar wavelets of the present embodiment, and other types of fuzzy models (such as the fuzzy relational model and Takagi-Sugeno model) could be substituted for or used in conjunction with the linguistic fuzzy model of the present embodiment. Furthermore, an absolute or other type of blink detection threshold could be specified if desired.

Figure 6:
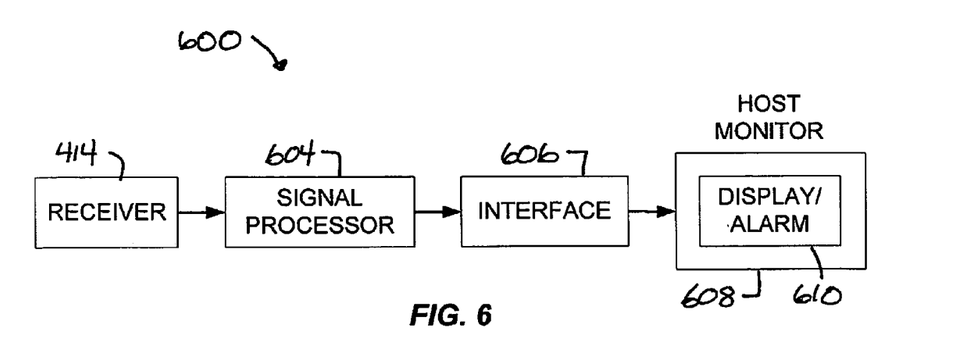
FIG. 6 illustrates an exemplary block diagram of a blink monitor, according an embodiment of the disclosure.

FIG. 6 illustrates an exemplary block diagram of a blink monitor 600, according an embodiment of the disclosure. As shown in FIG. 6, the blink monitor 600 includes the receiver 414, a signal processor 604, an interface 606 and a host monitor 609 including a display and/or alarm 610. As discussed in the foregoing, the receiver 414 is capable of, in some embodiments, wirelessly receiving blink sensor signal(s) indicative of electrical impulses in muscles indicative of eye blinking. The receiver 414 sends the blink sensor signal(s) to processing circuitry 604, which are capable of implementing the waveform processing software modules discussed with reference to FIG. 5. In an embodiment, a resulting drowsiness decision can be advantageously communicated via the interface 606 to the host monitor or monitoring device 608. In an embodiment, the drowsiness decision output from the DSP 604 is communicated via a standard hospital communication protocol, customized manufacturer protocol, or the like, to a hospital patient monitor. In another embodiment, the drowsiness decision output from the DSP 604 is communicated via a standard cellular or other network protocol to a personal emergency system, such as OnStar, to an emergency facility, such as the local police or fire station, to a management facility, or the like.

In yet another embodiment, the drowsiness decision output from the DSP 604 is communicated to an intelligent vehicle system. The drowsiness decision is important for monitoring driver vigilance/fatigue and driver distraction. For such commercial, military, or private vehicle systems, extreme drowsiness decision feedback will alert autonomous driving systems to avoid collisions and driver assistance systems to display alarms and other cues to increase driver awareness and/or inform management or emergency personnel. In another embodiment, the monitor 608 includes a plug-in module that communicates with a host device such as a personal computer, vehicle audio device, dedicated display, or the like.

An artisan will recognize that the interface 606 and host monitor 608 in FIG. 6 may be replaced by other components within a monitor, such as a standalone monitor. Rather than interfacing to other devices, the standalone monitor may comprise a receiver that sends received signals to a processor-based device adapted to process signals derived from one or more living subjects. In response to the drowsiness decision, the monitor outputs signals and alarms to its own display. In one exemplary embodiment, the standalone monitor mounts to a commercial, military, or private vehicle dashboard. When the monitor determines that the driver is becoming drowsy, is dangerously drowsy (i.e., an extreme drowsiness decision), or the like, the monitor loudly alarms, increases radio volume, activate vibration mechanisms in the vehicle seat, or the like in an effort to fully wake the driver.

In yet another embodiment, the monitor 608 comprises an ophthalmology disorder monitor. In such embodiments, EMG signals from both eyes are compared using the discrete wavelet transforms discussed in the foregoing. Moreover, the signal processing can be chosen from discrete wavelet transforms to produce spike clusters representing the onset of a blink or focus response. Disorder parameters obtained from convolution of the left and right EMG with wavelet and scaling filters are analyzed using the fuzzy model module 510. Based on current values of disorder parameters, time intervals are judged as being normal or representative of a least one disorder. For example, one set of input membership functions for the fuzzy model could be based on the similarity in the timing of the global minimum of the Haar wavelet approximation coefficients from both eyes, calculated between two blink onsets. In concert with a second set of input membership functions and a rule base inference table, a strabismus detection decision would be generated (on/off), based on one set of output membership functions. An artisan will recognize that clinical data will advantageously assist in determining the best or most appropriate particular values of the foregoing wavelets, input membership functions, rule base inference table, and output membership functions. The clinical data may advantageously include EMG patterns determined to correspond to particular patient conditions, including normals and the onset or occurrence of ophthalmology disorders.

In various embodiments, the ophthalmology disorder monitor may advantageously communicate with an accounting system to provide fee based determination of disorders, to track patient data, to collect clinical data, or the like. In an embodiment, the disorder comprises strabismus.

FIGS. 7($b$)-($c$) illustrate graphs of a blink EMG signal obtained from a subject in an alert state (FIG. 7($b$)) and the same subject in a drowsy state (FIG. 7($c$)). As shown in FIG. 7($c$), the blink EMGs include differing information that when evaluated, provide indicators of the alertness/drowsiness, ocular disorder or the like. For example, the duration of peaks, their frequency, their shape, the surrounding shapes, and the like all provide information usable to evaluate a condition of a person.

Although the foregoing invention has been described in terms of certain preferred embodiments, other embodiments will be apparent to those of ordinary skill in the art from the disclosure herein. For example, it is noted that while the disclosure described an apparatus and method for determining drowsiness suitable for use under the lower eyelash of a human subject, the invention may also conceivably be embodied or adapted to monitor drowsiness or another parameter derived from a biopotential at other locations on the human body, as well as monitoring drowsiness or another parameter derived from a biopotential on other warm-blooded species. Moreover, the blink sensors may comprise other sensors capable of outputting electrical signals indicative of blink occurrences, such as, for example, piezoelectric sensors or the like.

Additionally, other combinations, omissions, substitutions and modifications will be apparent to the skilled artisan in view of the disclosure herein. Accordingly, the present invention is not intended to be limited by the reaction of the preferred embodiments, but is to be defined by reference to the appended claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A method of determining a patient condition including at least one of drowsiness and ocular disorder, based on at least one blink electromyogram (EMG) signal measured from electrical activity in one or more muscles around at least one eye of the patient, the method comprising:
   receiving at least one blink EMG signal from a sensor capable of detecting electrical activity in one or more muscles in a body of a person, the electrical activity being indicative of a blink occurrences;
   determining which data from the blink EMG signal represents a plurality of the blink occurrences; and
   evaluating the plurality of blink occurrences represented by the data from the blink EMG signal to determine an onset or actual occurrence of a patient condition, wherein the patient condition includes at least one of drowsiness and an ocular disorder.

2. The method of claim 1, further comprising activating an alarm when the blink occurrence data indicates the onset or occurrence of drowsiness.

3. The method of claim 2, wherein the activating an alarm comprises activating at least one of an audio and visual alarm perceptible to the person to attempt to restore alertness.

4. The method of claim 2, wherein the activating an alarm comprises informing emergency personnel.

5. The method of claim 2, wherein the activating an alarm comprises informing management personnel.

6. The method of claim 2, wherein the activating an alarm comprises informing police personnel.

7. The method of claim 2, wherein the activating an alarm comprises informing a vehicle monitoring system.

8. The method of claim 1, further comprising informing a caregiver when the blink occurrence data indicates the onset or occurrence of the ocular disorder.

9. The method of claim 8, wherein the ocular disorder comprises strabismus.

10. The method of claim 1, wherein the receiving comprises wirelessly receiving.

11. A device for identifying a blink occurrence from at least one blink electromyogram (EMG) signal measured from electrical activity in one or more muscles around at least one eye, the device comprising:
    an electrode pair configured to be positioned with respect to one or more muscles used to blink at least one eye in order to output a blink EMG signal indicative of a changing biopotential associated with the one or more muscles; and
    a processing device configured to receive the blink EMG signal and identify a plurality of blink occurrences within data from the blink EMG signal and to determine a patient condition using at least a portion of data corresponding to the plurality of identified blink occurrences.

12. The device of claim 11, wherein the processing device further comprises a processor and a memory accessible by the processor configured to store instructions capable of causing the processor to filter the signal using wavelet transforms and to apply logic rules to the filtered signal to determine a patient condition.

13. The device of claim 12, wherein the patient condition comprises drowsiness.

14. The device of claim 12, wherein the patient condition comprises an ocular disorder.

15. The device of claim 12, wherein the wavelet transform comprises Haar coefficients.

16. The device of claim 12, wherein instructions are further capable of causing the process to evaluate blink-blink intervals.

17. The device of claim 11, further comprising an interface to a host monitor.

18. The device of claim 11, wherein the electrodes of the electrode pair are spaced about 0.875 of an inch from one another.

19. A blink monitoring system for processing a blink electromyogram (EMG) signal measured from electrical activity in one or more muscles around at least one eye, said system comprising:
    a sensor comprising an electrode pair capable of outputting a blink EMG signal indicative of an electrical biopotential from one or more muscles related to blink occurrences, a transmitting device capable of wirelessly transmitting the signal, and a flexible circuit housing the electrode and the transmitting device; and
    a monitor capable of determining where a plurality of the blink occurrences appear in the blink EMG signal, and using at least a portion of the signal where one or more of the plurality of the blink occurrences appear, determining a patient condition.

20. The blink monitoring system of claim 19, wherein the sensor further comprises a converter capable of converting the signal to digital data, wherein the transmitting device transmits the digital data.

21. The blink monitoring system of claim 19, wherein the sensor further comprises an amplifier capable of amplifying the signal.

22. The blink monitoring system of claim 19, wherein the electrode pair comprises a tab electrode.

23. The blink monitoring system of claim 19, wherein the electrodes of the electrode pair are spaced about one (1) cm from one another.

24. A monitor for monitoring the alertness of a person based on processing a blink electromyogram (EMG) signal measured from electrical activity in one or more muscles around at least one eye of a person, the monitor comprising:
    a sensor capable of detecting the blink EMG signal, the blink EMG signal being indicative of a blink occurrences;
    a receiver configured to receive data from said sensor indicative of the blink EMG signal of the a person responsive to said blink occurrences;
    a processor configured to determine a plurality of blink occurrences within the blink EMG signal and evaluate from the blink EMG signal where at least some of the plurality of blink occurrences appear to determine an onset or occurrence of diminished alertness; and
    an alarm signal capable of activating an alarm responsive to the onset or occurrence of the diminished alertness in the person.

25. The monitor of claim 24, wherein the monitor is adapted for use in a vehicle and the person comprises a driver.

26. The monitor of claim 25, wherein the alarm signal is provided to the vehicle and devices associated with the vehicle provide at least one of audio and visual alarm.

27. The monitor of claim 24, wherein the monitor is adapted for use in a vessel and the person comprises a captain.

28. The monitor of claim 24, wherein the monitor is adapted for use in an aircraft and the person comprises a pilot.

29. The monitor of claim 24, wherein the monitor is adapted for use in a combat setting and the person comprises a solider.

30. A monitoring device for monitoring the alertness of a person from blink electromyogram (EMG) data indicating blink occurrences from electrical activity in one or more muscles around at least eye of the person, said device comprising:

a sensor configured to detect at least one blink EMG signal from one or more muscles around at least one eye of a person indicating a set of blinks of the at least one eye; and a processor device configured to receive the at least one blink EMG signal from the sensor, identify a plurality of blink occurrences based on a wavelet transform of at least one conditioned signal responsive to said blink EMG signal, identify a pattern of blink-to-blink occurrences based on the transformed blink EMG signal, determine a condition of the person based on the identified pattern of blink-to-blink occurrences, and generate an output signal at least when the condition of the person indicates an onset or occurrence of diminished alertness in the user.

31. The monitoring device of claim 30, wherein the processor is configured to identify the plurality of blink occurrences based on a discrete wavelet transform.

32. The monitoring device of claim 30, wherein the processor comprises a wavelet filter that employs a set of Haar detail coefficients to isolate each onset of a blink occurrence.

33. The monitoring device of claim 30, wherein the processor comprises a highpass wavelet filter to isolate each onset of a blink occurrence.

34. The monitoring device of claim 30, wherein the processor comprises a lowpass scaling filter to isolate activity in the EMG signal between blink occurrences.

35. The monitoring device of claim 30, wherein the processor identifies the pattern of blink-to-blink occurrences based on time intervals between blinks.

* * * * *

UNITED STATES PATENT AND TRADEMARK OFFICE
CERTIFICATE OF CORRECTION

PATENT NO.      : 7,639,146 B2                                        Page 1 of 1
APPLICATION NO. : 11/235373
DATED           : December 29, 2009
INVENTOR(S)     : Gail D. Baura It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 345 days.

Signed and Sealed this

Twenty-first Day of December, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,639,146 B2 | Page 1 of 1 |
| APPLICATION NO. | : 11/235373 | |
| DATED | : December 29, 2009 | |
| INVENTOR(S) | : Gail D. Baura | |

It is certified that error appears in the above-identified patent and that said Letters Patent is hereby corrected as shown below:

Title Page; item (56);

At Page 2, column 2, line 18, under Other Publications, please change "D"Ophtamologie," to --D'Ophtalmologie,--.

At Col. 8, line 9, please change "A/C" to --ADC--.

At Col. 12, line 2 (Claim 12), please change "a" to --the--.

At Col. 12, line 53 (Claim 24), after "the" please delete "a".

At Col. 13, line 7 (Claim 29), please change "solider." to --soldier.--.

Signed and Sealed this
First Day of March, 2011

David J. Kappos
*Director of the United States Patent and Trademark Office*